(12) United States Patent
Murata et al.

(10) Patent No.: US 10,087,159 B2
(45) Date of Patent: Oct. 2, 2018

(54) METHOD FOR PRODUCING 3-CHLORO-2-HYDROXYPROPYL (METH)ACRYLATE AND METHOD FOR PRODUCING GLYCIDYL (METH)ACRYLATE

(71) Applicant: Mitsubishi Rayon Co., Ltd., Tokyo (JP)

(72) Inventors: Naoshi Murata, Hiroshima (JP); Hiroyuki Mori, Hiroshima (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 15/509,558

(22) PCT Filed: Aug. 4, 2015

(86) PCT No.: PCT/JP2015/072067
§ 371 (c)(1),
(2) Date: Mar. 8, 2017

(87) PCT Pub. No.: WO2016/047277
PCT Pub. Date: Mar. 31, 2016

(65) Prior Publication Data
US 2017/0305870 A1 Oct. 26, 2017

(30) Foreign Application Priority Data
Sep. 22, 2014 (JP) ................. 2014-192145

(51) Int. Cl.
C07D 301/16 (2006.01)
C07C 67/26 (2006.01)

(52) U.S. Cl.
CPC ............ *C07D 301/16* (2013.01); *C07C 67/26* (2013.01)

(58) Field of Classification Search
CPC .............................. C07D 301/16; C07C 67/26
See application file for complete search history.

(56) References Cited

FOREIGN PATENT DOCUMENTS

| JP | S48-011083 B1 | 4/1973 |
| JP | H07-002818 A | 1/1995 |
| JP | H07-118251 A | 5/1995 |
| JP | 2001-233868 A | 8/2001 |
| JP | 2003-055304 A | 2/2003 |
| JP | 2007-153853 A | 6/2007 |
| JP | 2010-531332 A | 9/2010 |
| WO | 2001/030881 A1 | 5/2001 |
| WO | 2009/000839 A1 | 12/2008 |
| WO | 2012/082400 A2 | 6/2012 |

OTHER PUBLICATIONS

International Search Report issued in corresponding International Patent Application No. PCT/JP2015/072067 dated Oct. 6, 2015.
Bukowska et al., "Synthesis of glycidyl esters," Journal of Chemical Technology and Biotechnology, 74: 1145-1148 (1999).
Otera et al., "A convenient synthesis of Glycidyl Esters (2,3-epoxypropyl alkanoates)," Synthesis, 1019-1020 (1986).
International Preliminary Report on Patentability and Written Opinion issued in corresponding PCT/JP2015/072067 dated Mar. 28, 2017

*Primary Examiner* — Timothy R Rozof
(74) *Attorney, Agent, or Firm* — Morgan, Lewis & Bockius LLP

(57) ABSTRACT

To reduce formation of side products and to enhance a selectivity rate in a method for producing 3-chloro-2-hydroxypropyl (meth)acrylate and in a method for producing glycidyl (meth)acrylate.
The present invention is characterized by a method for producing 3-chloro-2-hydroxypropyl (meth)acrylate through a reaction of (meth)acrylic acid and epichlorohydrin; more specifically, the reaction is carried out by using 0.5 to 2 mol of epichlorohydrin relative to 1 mol of (meth)acrylic acid, and by adding epichlorohydrin to (meth)acrylic acid in the presence of a catalyst. Also, the present invention is characterized by a method for producing glycidyl (meth)acrylate through a reaction of 3-chloro-2-hydroxypropyl (meth)acrylate and a basic carbonate compound in a polar solvent.

7 Claims, No Drawings

METHOD FOR PRODUCING 3-CHLORO-2-HYDROXYPROPYL (METH)ACRYLATE AND METHOD FOR PRODUCING GLYCIDYL (METH)ACRYLATE

TECHNICAL FIELD

The present invention relates to a method for producing 3-chloro-2-hydroxypropyl (meth)acrylate, and to a method for producing glycidyl (meth)acrylate.

BACKGROUND ART

In a method typically employed for synthesizing glycidyl (meth)acrylate, epichlorohydrin is used as raw material. Such synthesis may be roughly sorted into the two methods described below.

A first method is to synthesize glycidyl (meth)acrylate by reacting epichlorohydrin and an alkali metal salt of (meth)acrylic acid in the presence of a catalyst (Patent Literature 1); and a second method is to synthesize glycidyl (meth)acrylate by reacting epichlorohydrin and (meth)acrylic acid in the presence of a catalyst so as to generate 3-chloro-2-hydroxypropyl (meth)acrylate as an intermediate, which is then subjected to a ring-closing reaction (dehydrochlorination reaction) in an alkaline solution (Patent Literature 2).

CITATION LIST

Patent Literature

Patent Literature 1: JP H07-2818A
Patent Literature 2: JP H07-118251A

SUMMARY OF THE INVENTION

Problems to be Solved by the Invention

However, the method described in Patent Literature 1 requires a process and a facility for producing alkali metal salts of (meth)acrylic acid, thus increasing the production cost of glycidyl (meth)acrylate.

The method described in Patent Literature 2 is known to result in a lower yield than the method in Patent Literature 1 when producing glycidyl (meth)acrylate, because of the lower selectivity rates in a first phase conducted by reacting epichlorohydrin and (meth)acrylic acid as well as in a second phase conducted through a ring-closing reaction in an alkaline solution.

In addition, since epichlorohydrin as raw material contains highly reactive epoxy groups, various side reactions may progress. Thus, suppressing side reactions and reducing formation of resultant side reaction products are the issues to be solved. It has been desired to reduce formation of side-reaction products throughout the entire process.

Considering the above, the main objective of the present invention is to provide a method capable of reducing formation of side-reaction products, while enhancing selectivity during reactions, for producing 3-chloro-2-hydroxypropyl (meth)acrylate and glycidyl (meth)acrylate.

Solutions to the Problems

The inventors of the present invention have carried out intensive studies on problems associated with conventional technology and found that the above objective is achieved by reacting epichlorohydrin and (meth)acrylic acid under specific conditions. Accordingly, the present invention has been completed.

Namely, an aspect of the present invention is a method for producing 3-chloro-2-hydroxypropyl (meth)acrylate by reacting (meth)acrylic acid and epichlorohydrin. In such a method, 0.5 to 2 mol of epichlorohydrin per 1 mol of (meth)acrylic acid is set for a reaction, where epichlorohydrin is added to (meth)acrylic acid in the presence of a catalyst.

Also, another aspect of the present invention is a method for producing glycidyl (meth)acrylate by reacting 3-chloro-2-hydroxypropyl (meth)acrylate and a basic carbonate compound in a polar solvent.

Furthermore, yet another aspect of the present invention is a method for producing glycidyl (meth)acrylate including the following steps (1) and (2):

(1) a step for producing 3-chloro-2-hydroxypropyl (meth)acrylate through a reaction of 0.5 to 2 mol of epichlorohydrin per 1 mol of (meth)acrylic acid, by adding epichlorohydrin to (meth)acrylic acid in the presence of a catalyst; and (2) a step for producing glycidyl (meth)acrylate by reacting 3-chloro-2-hydroxypropyl (meth)acrylate and a basic carbonate compound in a polar solvent.

Effects of the Invention

According to the present invention, 3-chloro-2-hydroxypropyl (meth)acrylate and glycidyl (meth)acrylate are produced while formation of side products is low. Moreover, present invention provides a method that exhibits high selectivity during the reactions for producing 3-chloro-2-hydroxypropyl (meth)acrylate and glycidyl (meth)acrylate.

DETAILED DESCRIPTION OF THE EMBODIMENTS

In the present application, (meth)acrylic acid indicates methacrylic acid or acrylic acid.

According to the present invention, glycidyl (meth)acrylate is obtained through a pathway for producing 3-chloro-2-hydroxypropyl (meth)acrylate. Hereinafter, a step for producing 3-chloro-2-hydroxypropyl (meth)acrylate is referred to as "step 1" and a step for producing glycidyl (meth)acrylate is referred to as "step 2."

[Step 1]: Producing 3-chloro-2-hydroxypropyl (meth)acrylate

In step 1, 3-chloro-2-hydroxypropyl (meth)acrylate is produced by reacting epichlorohydrin and (meth)acrylic acid.

Reaction conditions specified as conditions (A) and (B) below are employed for the above reaction.

Condition (A): the reaction is carried out by setting the amount of epichlorohydrin at 0.5 to 2 mol per 1 mol of (meth)acrylic acid.

Condition (B): epichlorohydrin is added to (meth)acrylic acid in the presence of a catalyst.

[Condition (A)]

When (meth)acrylic acid and epichlorohydrin are reacted, the molar ratio is set at 0.5 to 2 mol of epichlorohydrin per 1 mol of (meth)acrylic acid. The ratio of epichlorohydrin relative to 1 mol of (meth)acrylic acid is preferred to be 0.6 to 1.5 mol, more preferably 0.8 to 1.2 mol. Relative to 1 mol of (meth)acrylic acid, a molar ratio of epichlorohydrin set at 0.5 mol or higher suppresses side reactions, while a molar ratio of epichlorohydrin set at 2 mol or lower also suppresses side reactions.

[Condition (B)]

In the present invention, epichlorohydrin is added to (meth)acrylic acid in the presence of a catalyst. More specifically, it is preferred to drop epichlorohydrin into a reaction vessel where (meth)acrylic acid and a catalyst have been charged and heated. According to such a method, the reaction is progressed safely at a high selectivity rate, while formation of side products is suppressed. By contrast, if epichlorohydrin and a catalyst are charged in a reaction vessel and heated, and then (meth)acrylic acid is dropped into the reaction vessel, formation of diesters increases, resulting in a lower selectivity rate.

[Other Conditions]

In step 1, the reaction temperature is preferred to be set at 50 to 150° C., more preferably 60 to 130° C. A reaction temperature of 50° C. or higher contributes to an efficient production of 3-chloro-2-hydroxypropyl (meth)acrylate. A reaction temperature of 150° C. or lower suppresses side reactions such as polymerization of 3-chloro-2-hydroxypropyl (meth)acrylate.

In step 1, the reaction time is not limited to any specific duration, and is selected appropriately according to the amount of raw material, reaction temperature and so on. For example, the reaction time is set for 0.1 to 20 hours, preferably 0.2 to 10 hours, more preferably 0.5 to 5 hours. By setting the reaction time to be 0.1 hour or longer, the reaction product is obtained at a higher conversion rate. By setting the reaction time to be 20 hours or shorter, formation of side products is suppressed.

[Catalyst]

Any known catalyst may be used as the catalyst in the reaction of step 1, for example, quaternary ammonium salts or ion-exchange resins having such salts. Examples of quaternary ammonium salts are tetraalkylammonium salts such as tetramethylammonium chloride, tetramethylammonium bromide, tetraethylammonium chloride, tetraethylammonium bromide, tetrabutyl ammonium chloride and tetrabutylammonium bromide. A commercially available strong basic anion exchange resin may be used as the ion-exchange resin. These catalysts may be used alone, or in combination thereof.

The amount of catalyst is not limited specifically. For example, relative to 1 mol of (meth)acrylic acid, the amount may be set at 0.0001 to 0.1 mol, preferably 0.0005 to 0.05 mol, more preferably 0.001 to 0.03 mol. Relative to 1 mol of (meth)acrylic acid, an amount of catalyst at 0.0001 mol or greater enhances the reaction rate, while an amount of catalyst at 0.1 mol or less suppresses formation of side products.

[Step 2]: Producing Glycidyl (meth)acrylate

In step 2, a reaction of 3-chloro-2-hydroxypropyl (meth)acrylate and a basic carbonate compound is carried out in a polar solvent to produce glycidyl (meth)acrylate. By using a specific kind of basic carbonate compound and a polar solvent as the solvent, side reactions are suppressed, thus reducing formation of side products.

The 3-chloro-2-hydroxypropyl (meth)acrylate produced in step 1 may be used as is, or it may be refined by a known method. Alternatively, 3-chloro-2-hydroxypropyl (meth)acrylate obtained by another method or a commercially available kind may be refined and used if applicable.

[Polar Solvent]

Examples of a polar solvent are alcohols, ketones, esters, amides, ethers, halogenated hydrocarbons, dialkyl sulfoxides and the like. Among them, alcohols are especially preferable.

[Alcohol]

An alcohol as the solvent is not limited to any specific kind. Considering availability and solubility, it is preferred to use a C1~C10 aliphatic hydrocarbon alcohol, more preferably a C1~C8 aliphatic hydrocarbon alcohol. Examples of such alcohols are methanol, ethanol, 1-propanol, 2-propanol, 1-butanol, 2-butanol, t-butanol, 1-heptanol, 1-hexanol, cyclohexanol, 1-pentanol, 1-octanol, and the like. Considering the boiling point and availability, 1-propanol, 2-propanol, 1-butanol, 2-butanol, t-butanol and the like are more preferable. Alcohols may be used alone or in combination thereof.

It is sufficient if there is enough alcohol to fluidize a salt side product into slurry. An alcohol is preferred to be used 0.1 to 100 times, more preferably 0.5 to 50 times, even more preferably 1 to 20 times, the mass of 3-chloro-2-hydroxypropyl (meth)acrylate. By setting the amount of alcohol to be at least 0.1 times the mass of 3-chloro-2-hydroxypropyl (meth)acrylate, the salt side product is efficiently fluidized. By setting the amount of alcohol to be no greater than 100 times the mass of 3-chloro-2-hydroxypropyl (meth)acrylate, glycidyl (meth)acrylate is efficiently refined or the like.

[Basic Carbonate Compound]

A basic carbonate compound is not limited to any specific kind as long as it is capable of promoting dehydrochlorination reactions of 3-chloro-2-hydroxypropyl (meth)acrylate. As for a basic carbonate compound, those containing Group 1 or Group 2 metals are preferred because they are capable of efficiently progressing reactions, suppressing side reactions and reducing formation of side products.

Examples of such a basic carbonate compound are lithium carbonate, sodium carbonate, potassium carbonate, rubidium carbonate, cesium carbonate, magnesium carbonate, calcium carbonate, and the like. Among them, potassium carbonate, rubidium carbonate, cesium carbonate and the like are more preferable. Those basic compounds may be used alone or in combination thereof.

The amount of basic carbonate compound is not limited specifically, as long as reactions are progressed efficiently. For example, relative to 1 mol of 3-chloro-2-hydroxypropyl (meth)acrylate, the amount is preferred to be 0.1 to 3 mol, more preferably 0.3 to 2 mol, even more preferably 0.5 to 1.5 mol. Relative to 1 mol of 3-chloro-2-hydroxypropyl (meth)acrylate, an amount of basic carbonate compound set at 0.1 mol or greater enhances the reaction rate, while an amount of basic carbonate compound set at 3 mol or less suppresses side reactions.

[Reaction Conditions]

The reaction temperature in step 2 is preferred to be 50 to 150° C., more preferably 60 to 130° C. A reaction temperature of 50° C. or higher contributes to efficiently producing glycidyl (meth)acrylate, while a reaction temperature of 150° C. or lower suppresses side reactions such as polymerization.

In step 2, the reaction time is not limited to any specific duration, and is selected appropriately according to the amount of raw material, reaction temperature and so on. For example, the reaction time is set to be 0.1 to 20 hours, preferably 0.2 to 10 hours, more preferably 0.5 to 5 hours. By setting a reaction time to be 0.1 hour or longer, glycidyl (meth)acrylate is obtained at a higher conversion rate. By setting the reaction time to be 20 hours or shorter, formation of side products is suppressed.

[Polymerization Inhibitor, Refining or the like]

A known polymerization inhibitor may be used to suppress polymerization in steps 1 and 2. Examples of a polymerization inhibitor are phenol-based inhibitors such as hydroquinone and p-methoxyphenol; amine-based inhibitors such as phenothiazine; and N-oxyl-based inhibitors such as 4-hydroxy-2,2,6,6-tetramethylpiperidine-N-oxyl (HO-TEMPO). They may be used alone or in combination thereof.

The amount of polymerization inhibitor is preferred to be 10 to 10000 mass ppm, more preferably 50 to 5000 mass ppm, relative to the mass of (meth)acrylic acid in step 1 and relative to the mass of 3-chloro-2-hydroxypropyl (meth)acrylate in step 2. By setting the amount of polymerization inhibitor to be at least 10 mass ppm, polymerization is sufficiently suppressed, while by setting the amount to be no greater than 10000 mass ppm, a decrease in quality, for example, coloration of products, is prevented.

To prevent polymerization, it is preferred to carry out reactions while introducing bubbles of oxygen or a gas containing oxygen such as air.

Also, glycidyl (meth)acrylate related to the present invention may be extracted or refined if applicable. Extraction and refining are not limited to any specific methods, and any known methods may be used. For example, the salt in a reaction mixture obtained in step 2 may be washed with water to remove unwanted components. Alternatively, the reaction mixture may be filtered to remove unwanted components. After washing with water or filtering, crude glycidyl (meth)acrylate contained in a solution is extracted through distillation so that highly purified glycidyl (meth)acrylate is obtained.

EXAMPLES

In the following, the present invention is described in detail by referring to the examples. However, the present invention is not limited to those examples. The compound in each of examples and comparative examples was analyzed through gas chromatography (GC). Example 1 relates to the production of 3-chloro-2-hydroxypropyl (meth)acrylate, and Examples 2-4 relate to the production of glycidyl (meth)acrylate.

Example 1

A 300-mL four-necked flask equipped with a thermometer, an air inlet tube, a stirring blade, a dropping funnel and a cooling tube was prepared and charged with 86.09 grams (1.0 mol) of methacrylic acid, 0.01 grams of an HO-TEMPO benzoate as the polymerization inhibitor, and 0.548 grams (0.005 mol) of tetramethylammonium chloride as the catalyst. In the dropping funnel, 101.78 grams (1.1 mol) of epichlorohydrin was filled.

Air was introduced into the flask at a rate of 10 mL/min., and the mixture in the flask was heated to 90° C. using an oil bath while being stirred. The epichlorohydrin started dropping when the temperature of the mixture reached 90° C., and dropped out into the flask in an hour. After the completion of dropping, the reaction mixture was stirred for 4 hours while its temperature was kept at 90° C.

When the reaction mixture was analyzed by GC, peak area percentages (%) of the composition were 84.612% of 3-chloro-2-hydroxypropyl methacrylate, 0.975% of glycidyl methacrylate, 1.106% of methacrylic acid, 4.450% of epichlorohydrin, 5.115% of diester, 0.364% of triester, 3.377% of 1,3-dichloro-2-propanol, 0.001% of glycidol, and 0.000% of dichloropropyl methacrylate. The results are shown in Table 1.

Comparative Examples 1 and 2

In Comparative Examples 1 and 2, the amounts of epichlorohydrin were changed to 208.19 grams (2.25 mol) and 416.37 grams (4.5 mol) respectively, and the epichlorohydrin amounts were each added to the four-neck flask all at once. The rest of the reactions were carried out the same as in Example 1. The results are shown in Table 1.

Comparative Example 3

The methacrylic acid in the four-neck flask was replaced with epichlorohydrin, and the epichlorohydrin in the dropping funnel was replaced with methacrylic acid. Then, methacrylic acid was dropped into epichlorohydrin through the dropping funnel. The rest of the reaction was carried out the same as in Example 1. The results are shown in Table 1.

Comparative Example 4

The reaction was carried out the same as in Example 1 except that the amount of epichlorohydrin charged in the dropping funnel was changed to 277.590 grams (3.0 mol). The results are shown in Table 1.

Comparative Example 5

When the reaction was initiated the same as in Example 1 except that epichlorohydrin was added to the four-neck flask all at once, the temperature of the reaction mixture rose to 186° C. in an early stage of the reaction, causing a reflux of the mixture. Accordingly, the reaction was observed to be out of control. Since the ratio of "methacrylic acid to epichlorohydrin" was "1:1.1", which means the amount of epichlorohydrin was less than those in Comparative Examples 1 and 2, there was no dilution effect derived from epichlorohydrin. Therefore, it is assumed that the reactions progressed fast, leaving no time to reduce the heat. Side products were 12.548% of 1,3-dichloropropanol and 23.586% of diester. The results are shown in Table 1.

TABLE 1

| | Reaction conditions | | Composition of reaction mixture (GC: area percentage) (%) | | | | | | | | |
|---|---|---|---|---|---|---|---|---|---|---|---|
| | methacrylic acid:epichlorohydrin (molar ratio) | dropping funnel | epichloro-hydrin | glyci-dol | glycidyl meth-acrylate | meth-acrylic acid | 1,3-dichloro-2-propanol | dichloro-propyl methacrylate | 3-chloro-2-hydroxypropyl methacrylate | tri-ester | di-ester |
| Example 1 | 1:1.1 | epichloro-hydrin | 4.450 | 0.001 | 0.975 | 1.106 | 3.377 | 0.000 | 84.612 | 0.364 | 5.115 |

TABLE 1-continued

| | Reaction conditions | | Composition of reaction mixture (GC: area percentage) (%) | | | | | | | |
|---|---|---|---|---|---|---|---|---|---|---|
| | methacrylic acid:epichlorohydrin (molar ratio) | dropping funnel | epichloro-hydrin | glyci-dol | glycidyl meth-acrylate | meth-acrylic acid | 1,3-dichloro-2-propanol | dichloro-propyl methacrylate | 3-chloro-2-hydroxypropyl methacrylate | tri-ester | di-ester |
| Comp. Example 1 | 1:2.25 | — | 23.520 | 0.409 | 25.444 | 0.000 | 13.287 | 1.380 | 35.534 | 0.019 | 0.407 |
| Comp. Example 2 | 1:4.5 | — | 52.692 | 0.375 | 23.298 | 0.000 | 11.135 | 1.086 | 11.238 | 0.007 | 0.169 |
| Comp. Example 3 | 1:1.1 | methacrylic acid | 1.609 | 0.000 | 3.745 | 0.280 | 10.294 | 0.273 | 57.873 | 0.473 | 25.453 |
| Comp. Example 4 | 1:3 | epichloro-hydrin | 38.239 | 0.521 | 27.472 | 0.000 | 13.103 | 1.404 | 18.740 | 0.167 | 0.354 |
| Comp. Example 5 | 1:1.1 | — | 0.373 | 0.001 | 1.792 | 0.018 | 12.548 | 0.000 | 61.051 | 0.632 | 23.586 |

Example 2

A 100-mL four-necked flask equipped with a thermometer, an air inlet tube, a stirring blade, and a cooling tube was prepared and charged with 5 grams of the reaction mixture containing 3-chloro-2-hydroxypropyl methacrylate (0.0264 mol of 3-chloro-2-hydroxypropyl methacrylate) obtained in Example 1, 20 grams of isopropyl alcohol (IPA) as the solvent, 2.737 grams (0.0198 mol) of potassium carbonate as the basic carbonate compound, and 0.001 grams of an HO-TEMPO benzoate as the polymerization inhibitor.

The mixture was heated to a temperature of 80° C. while being stirred, and the reaction was carried out for 2 hours.

The obtained reaction mixture was analyzed by GC. The area percentages (%) of the composition were 2.375% of 3-chloro-2-hydroxypropyl methacrylate, 89.149% of glycidyl methacrylate, 0.000% of methacrylic acid, 6.087% of diester, 1.341% of triester, 0.011% of 1,3-dichloro-2-propanol, 1.055% of glycidol, and 0.000% of dichloropropyl methacrylate. The results are shown in Table 2.

Examples 3 and 4

Reactions were carried out the same as in Example 2 except that rubidium carbonate and cesium carbonate were respectively used as the basic carbonate compound. The results are shown in Table 2.

Comparative Examples 6 and 7

Reactions were carried out the same as in Example 2 except that dimethylformamide (DMF) and epichlorohydrin (EPC) were used respectively as the solvent. The results are shown in Table 2.

Comparative Examples 8-12

Reactions were carried out the same as in Example 2 except that basic compounds specified in Table 2 were respectively used. The results are shown in Table 2.

TABLE 2

| | Reaction conditions | | Composition of reaction mixture (GC: area percentage) (%) | | | | | | | |
|---|---|---|---|---|---|---|---|---|---|---|
| | solvent | basic compound carbonate | glycidol | glycidyl methacrylate | methacrylic acid | 1,3-dichloro-2-propanol | dichloropropyl methacrylate | 3-chloro-2-hydroxypropyl methacrylate | triester | diester |
| Example 2 | IPA | $K_2CO_3$ | 1.055 | 89.149 | 0.000 | 0.011 | 0.000 | 2.357 | 1.341 | 6.087 |
| Example 3 | IPA | $Rb_2CO_3$ | 2.550 | 86.715 | 0.000 | 0.021 | 0.021 | 0.986 | 2.950 | 6.757 |
| Example 4 | IPA | $Cs_2CO_3$ | 2.910 | 88.950 | 0.000 | 0.064 | 0.000 | 1.456 | 0.318 | 6.302 |
| Comp. Example 6 | DMF | $K_2CO_3$ | 1.155 | 56.493 | 0.000 | 0.080 | 0.343 | 10.599 | 0.611 | 30.719 |
| Comp. Example 7 | EPC | $K_2CO_3$ | 1.614 | 64.469 | 0.000 | 11.734 | 1.145 | 16.973 | 0.351 | 3.714 |
| Comp. Example 8 | IPA | $LiOH \cdot H_2O$ | 15.640 | 30.363 | 0.000 | 3.553 | 0.000 | 20.457 | 19.469 | 10.518 |
| Comp. Example 9 | IPA | NaOH | 3.707 | 54.471 | 0.000 | 0.648 | 0.011 | 27.676 | 3.632 | 9.855 |
| Comp. Example 10 | IPA | KOH | 4.557 | 73.489 | 0.000 | 0.211 | 0.000 | 3.028 | 4.389 | 14.326 |
| Comp. Example 11 | IPA | DMAP | 0.007 | 3.951 | 1.855 | 3.971 | 0.000 | 83.633 | 0.868 | 5.715 |
| Comp. Example 12 | IPA | $Et_3N$ | 0.503 | 11.704 | 4.788 | 1.425 | 0.000 | 73.388 | 0.784 | 7.408 |

INDUSTRIAL APPLICABILITY

Glycidyl (meth)acrylate produced by the method related to the present invention is suitable as raw material for various coatings, adhesives and binders as well as for a monomer to be used in various reactions.

What is claimed is:

1. A method for producing glycidyl (meth)acrylate, comprising:
   (1) a step of dropping epichlorohydrin into (meth)acrylic acid in the presence of a catalyst to provide 3-chloro-2-hydroxypropyl (meth)acrylate, where 0.5 to 2 mol of the epichlorohydrin is reacted per 1 mol of the (meth)acrylic acid; and (2) a step for producing glycidyl (meth)acrylate by reacting the 3-chloro-2-hydroxypropyl (meth)acrylate with a basic carbonate compound in a polar solvent.

2. The method for producing glycidyl (meth)acrylate according to claim 1, wherein the polar solvent is an alcohol.

3. The method for producing glycidyl (meth)acrylate according to claim 2, wherein the alcohol is a C1-C10 aliphatic hydrocarbon alcohol.

4. The method for producing glycidyl (meth)acrylate according to claim 2, wherein the alcohol is at least one kind selected from the group consisting of 1-propanol, 2-propanol, 1-butanol, 2-butanol and t-butanol.

5. The method for producing glycidyl (meth)acrylate according to claim 1, wherein the basic carbonate compound comprises a Group 1 or Group 2 metal.

6. The method for producing glycidyl (meth)acrylate according to claim 1, wherein the basic carbonate compound is at least one kind selected from the group consisting of potassium carbonate, rubidium carbonate and cesium carbonate.

7. The method for producing glycidyl (meth)acrylate according to claim 5, wherein the basic carbonate compound is at least one kind selected from the group consisting of potassium carbonate, rubidium carbonate and cesium carbonate.

* * * * *